(12) United States Patent
Cordero Otero et al.

(10) Patent No.: US 7,531,348 B2
(45) Date of Patent: May 12, 2009

(54) RECOMBINANT YEAST FOR LIGNOCELLULOSE RAW MATERIALS

(75) Inventors: Ricardo Roman Cordero Otero, Stellenbosch (ZA); Bärbel Hahn-Hägerdal, Lund (SE); Willhem Herber Van Zyl, Stellenbosch (ZA)

(73) Assignee: Scandinavian Technology Group AB, Lund (SE)

( * ) Notice: Subject to any disclaimer, the term of this patent is extended or adjusted under 35 U.S.C. 154(b) by 0 days.

(21) Appl. No.: 10/293,255

(22) Filed: Nov. 14, 2002

(65) Prior Publication Data

US 2003/0157675 A1      Aug. 21, 2003

(51) Int. Cl.
  *C12N 1/14*    (2006.01)
  *C12N 9/02*    (2006.01)
  *C12N 9/04*    (2006.01)
  *C12N 9/12*    (2006.01)
  *C12N 1/20*    (2006.01)
  *C12N 15/00*   (2006.01)
  *C07H 21/04*   (2006.01)
  *C12N 9/00*    (2006.01)
  *C12N 15/01*   (2006.01)
  *C12Q 1/00*    (2006.01)
  *C12Q 1/68*    (2006.01)
  *C12P 21/04*   (2006.01)

(52) U.S. Cl. ............ 435/254.21; 435/4; 435/6; 435/69.1; 435/71.1; 435/440; 435/189; 435/190; 435/194; 435/183; 435/252.3; 435/320.1; 435/254.1; 435/441; 536/23.2

(58) Field of Classification Search ......... 435/189, 435/190, 194, 252.3, 254.1, 254.21, 320.1, 435/440, 441; 536/23.2, 23.74
See application file for complete search history.

(56) References Cited

U.S. PATENT DOCUMENTS 5,789,210 A * 8/1998 Ho et al. .............. 435/163
6,271,007 B1 * 8/2001 Apajalahti et al. ..... 435/137
6,410,302 B1   6/2002 Träff et al. ............ 435/254.2
7,381,551 B2 * 6/2008 Wahlbom et al. ...... 435/161

FOREIGN PATENT DOCUMENTS

WO    WO 95/13362    5/1995
WO    WO 97/42307    11/1997

OTHER PUBLICATIONS

Olsson et al. Enzyme and Microbial Technology 18:312-331, 1996.*

* cited by examiner

*Primary Examiner*—Yong D Pak
(74) *Attorney, Agent, or Firm*—Finnegan, Henderson, Farabow, Garrett & Dunner, L.L.P.

(57) ABSTRACT

The present invention relates to a method for obtaining a recombinant yeast of *Saccharomyces cerevisiae*, which ferments lignocellulose raw materials to ethanol, including introducing DNA into a yeast so as to cause the yeast to have introduced genes encoding xylose reductase, xylitol dehydrogenase and xylulokinase.

17 Claims, 1 Drawing Sheet

RECOMBINANT YEAST FOR LIGNOCELLULOSE RAW MATERIALS

FIELD OF INVENTION

The present invention relates to a method of obtaining yeast for fermentation of lignocellulose raw materials and a recombinant yeast for fermentation of lignocellulose raw materials.

BACKGROUND TO INVENTION AND DESCRIPTION OF PRIOR ART

Lignocellulose is the main component of forest product residues and agricultural waste. Lignocellulosic raw materials are mainly composed of cellulose, hemicellulose, and lignin. The cellulose fraction is made up of glucose polymers, whereas the hemicellulose fraction is made up of a mixture of glucose, galactose, mannose, xylose and arabinose polymers. The lignin fraction is a polymer of phenolic compounds. Xylose is found in hardwood and softwood hemicelluloses, whereas arabinose is a component in hemicellulose in certain agricultural crops, such as corn.

The cellulose and hemicellulose fractions can be hydrolyzed to monomeric sugars, which can be fermented to ethanol. Ethanol can serve as an environmentally acceptable liquid fuel for transportation, since carbon dioxide released in the fermentation and combustion processes will be sorbed by growing plants in forests and fields.

The price for lignocellulose-derived ethanol has been estimated by Von Sivers, M., G. Zacchi, L. Olsson, and B. Hahn-Hägerdal. 1994. 'Cost analysis of ethanol production from willow using recombinant *Escherichia coli*.' Biotechnol. Prog. 10:555-560. Their calculations were based on the fermentation of all hexose sugars (glucose, galactose and mannose) to ethanol and they estimated that the fermentation of pentose sugars (xylose and arabinose) to ethanol could reduce the price of ethanol by approximately 25%. The microbial conversion of lignocellulosic derived hexoses and pentoses would therefore not only be environmentally acceptable, but could also be cost-effective.

Further, the release of monomeric sugars from lignocellulosic raw materials also release by-products, such as weak acids, furans and phenolic compounds, which are inhibitory to the fermentation process. The commonly used Baker's yeast, *Saccharomyces cerevisiae*, is the only ethanol producing microorganism that is capable of efficiently fermenting non-detoxified ligocellulose hydrolysates (Oisson and Hahn-Hägerdal, "Fermentation of lignocellulosic hydrolysates for ethanol production", Enzyme Microbial Technol. 18;312-331, 1996). Particularly, efficient fermenting strains of *Saccharomyces cerevisiae* have been isolated from the fermentation plant at a pulp and paper mill (Lindén et al., "Isolation and characterization of acetic acid-tolerant galactose-fermenting strains of *Saccharomyces cerevisiae* from a spent sulfite liquor fermentation plant", Appl. Environ. Microbiol. 158:1661-1669, 1992).

*Saccharomyces cerevisiae* ferments the hexose sugars glucose, galactose and mannose to provide ethanol, but is unable to ferment the pentose sugars xylose and arabinose due to the lack of one or more enzymatic steps. *Saccharomyces cerevisiae* can ferment xylulose, an isomerization product of xylose, to ethanol (Wang et al., "Fermentation of a pentose by yeasts", Biochem. Biophys. Res. Commun. 94:248-254, 1980; Chiang et al., "D-Xylulose fermentation to ethanol by *Saccharomyces cerevisiae*", Appl Environ. Microbiol. 42:284-289, 1981; Senac and Hahn-Hägerdal, "Intermediary metabolite concentrations in xylulose- and glucose-fermenting *Saccharomyces cerevisiae* cells", Appl. Environ. Microbiol. 56:120-126, 1990).

In eukaryotic cells, the initial metabolism of xylose is catalyzed by a xylose reductase (XR), which reduces xylose to xylitol, and a xylitol dehydrogenase (XDH), which oxidizes xylitol to xylulose. Xylulose is phosphorylated to xylulose 5-phosphate by a xylulose kinase (XK) and further metabolized through the pentose phosphate pathway and glycolysis to ethanol.

*Saccharomyces cerevisiae* has been genetically engineered to metabolize and ferment xylose. The genes for XR and XDH from the xylose-fermenting yeast *Pichia stipitis* have been expressed in *Saccharomyces cerevisiae* (European Patent to C. Hollenberg, 1991; Hallborn et al., "Recombinant yeasts containing the DNA sequences coding for xylose reductase and xylitol dehydrogenase enzymes", W091/15588; Kötter and Ciriacy, "Xylose fermentation by *Saccharomyces cerevisiae*", Appl. Microbiol. Biotechnol. 38:776-783: 1993). The transformants metabolize xylose but do not ferment the pentose sugar to ethanol.

The gene for xylulose kinase (M) from *Saccharomyces cerevisiae* has been cloned and overexpressed in XR-XDH-expressing transformants of *Saccharomyces cerevisiae* (Deng and Ho, "Xylulokinase activity in various yeasts including *Saccharomyces cerevisiae* containing the cloned xylulokinase gene", Appl. Biochem. Biotechnol. 24/25:193-199, 1990; Ho and Tsao, "Recombinant yeasts for effective fermentation of glucose and xylose", W095/13362, 1995; Moniruzzarnan et al., "Fermentation of corn fibre sugars by an engineered xylose utilizing a *Saccharomyces* strain", World J. Microbiol. Biotechnol. 13:341-346, 1997). These strains have been shown to produce net quantities of ethanol in fermentations of mixtures of xylose and glucose. Using the well established ribosomal integration protocol, the genes have been chromosomally integrated to generate strains that can be used in complex media without selection pressure (Ho and Chen, "Stable recombinant yeasts for fermenting xylose to ethanol", W09/42307; Toon et al., "Enhanced cofermentation of glucose and xylose by recombinant *Saccharomyces* yeast strains in batch and continuous operating modes", Appl. Biochem. Biotechnol. 63/65:243-255,1997).

Although great strides hare been made, there exists a need in the art for a method of, and a tool for efficiently fermenting lignocellulose hydrolysates to produce ethanol.

SUMMARY OF INVENTION

According to the invention, a method for obtaining a recombinant yeast, which ferments lignocellulose raw materials to ethanol, includes introducing DNA into a yeast so as to cause the yeast to have introduced genes encoding xylose reductase, xylitol dehydrogenase and xylulokinase.

The yeast may be capable of producing lignocellulose-utilizing enzyme selected from the group of xylose reductase (XR), xylitol dehydrogenase (XD), and xylulokinase (XK).

The yeast may be of the genus *Saccharomyces cerevisiae* and *Pichia stipitis*.

The lignocellulose utilizing enzyme xylose reductase (XR) may be obtained from *Pichia stipitis*.

The lignocellulose utilizing enzyme xylitol dehydrogase (XID) may obtained from *Pichia stipitis*.

The lignocellulose utilizing enzyme xylulokinase (XK) may be obtained from *Saccharomyces cerevisiae*.

The method may include isolating suitable mutants by ethyl methanesulphonate (EMS) treatment.

The mutant may be a xylose-fermenting mutant XYL 125.
The mutant may be a xylose-fermenting mutant XYL 145.
The invention also extend to a recombinant yeast containing introduced genes encoding xylose reductase, xylitol dehydrogenase and xylulokinase.

BRIEF DESCRIPTION OF DRAWINGS

The present invention will now be described by way of examples with reference to the accompanying drawings, in which there is shown in.

DETAILED DESCRIPTION OF THE DRAWINGS

Figure 1:
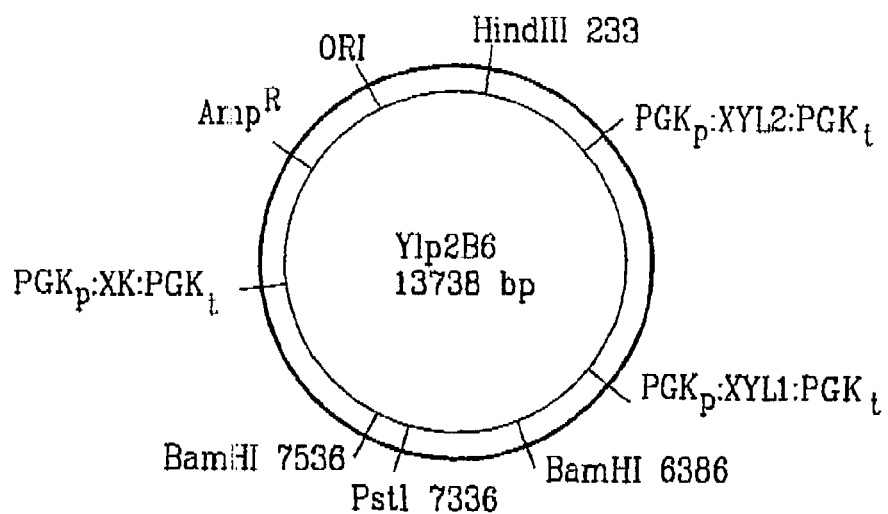
FIG. 1 is a schematic presentation of the present invention, indicating the physical map of the expression vector Yip2B6 containing the *Pichia stipitis* genes XYL1 and XYL2 encoding XR and XDH, and *Saccharomyces cerevisiae* gene XK encoding XK. PGKp=PGK promoter; $PGK_t$=PGK terminator.

According to the invention there is provided a method for providing a microorganism with the capability of efficiently fermenting lignocellulose raw materials to produce ethanol. The method provides the steps of
  transforming the microorganism with a nucleotide sequence comprising genes which encode certain xylose degrading enzymes; and
  a promoter for promoting transcription of these genes in the transformed microorganism and production of these enzymes.

If required to effect synthesis and secretion of these enzymes by the microorganism, the nucleotide sequences can further include suitable leader sequences for these genes.

The microorganism is a yeast strain, and the method provides the yeast strain with the capability of producing at least one of the following lignocellulose utilising enzymes:
  xylose reductase (XR);
  xylitol dehydrogenase (XD); and
  xylulokinase (XK)

The invention further includes a method for fermenting lignocellulosic raw materials with a microorganism which has been transformed into a xylose-utilising microorganism by introducing into the microorganism
  DNA comprising genes which encode xylose utilising enzymes; and
  a promoter for promoting transcription of these genes in the microorganism and production of these enzymes.

The recombinant DNA for use in transforming a microorganism so as to provide it with a capability of fermenting lignocellulose raw materials, said DNA comprising of
  genes encoding xylose utilising enzymes; and
  a promoter for promoting transcription of these genes in the transformed microorganism and production of these enzymes.

The xylose reductase (XR), xylitol dehydrogenase (XD) and xylulokinase (XK) genes which encode the xylose utilising enzymes may be obtained from the following microorganisms:
  *Pichia stipitis* (for XR and XD genes)
  *Saccharomyces cerevisiae* (for XK gene)

The method for providing a microorganism also encompasses the isolation of mutants on the basis of their ability to grow rapidly on xylose and the characterization of selected strains, said method comprising ethyl methanesulphonate (EMS) treatment.

The mutants are XYL125 and XYL145 and can effectively utilise xylose in the absence of other carbon sources.

It will be appreciated that the recombinant yeasts, mutants, DNA molecules and vectors comprising xylose reductase (XR), xylitol dehydrogenase (XD) and xylulokinase (XK) genes, which the present invention provides, are well known to occur in a wide variety of microorganisms and that numerous XR, XD and XK genes have in fact been identified and isolated. The particular source of these genes is not critical to the broad aspects of this invention, as long as the enzymes have occurring XR, XD and XK activity. Further, these genes may be obtained as naturally occurring XR, XD and XK genes, or be modified, or be synthesized by any techniques known in the current state of the art.

The present invention further provides one or more promoters and/or leader sequences for promoting transcription of the genes and production of the enzymes.

A preferred expression vector comprises the xylose reductase- and xylitol dehydrogenase genes from *Pichia stipitis*, and a xylulokinase gene from *Saccharomyces cerevisiae* (together with suitable promoters and possibly leader sequences), which when transformed into *Saccharomyces cerevisiae*, will enable it to utilise xylose.

Legal deposits under the regulations of the Budapest Treaty were made of the *Saccharomyces cerevisiae* transgenic strain (XYLUSM21) as well as the two mutants (XYLUSM125, XYLUSM145) at the Centraalbureau voor Scimmelcultures (CBS) Baarn $ Delft, The Netherlands. The depositions were made on the 1st of May, 2000 under the deposition numbers CBS 102678 (XYLUSM21), CBS 102679 (XYLUSM125), and CBS 102680 (XYLUSM145), respectively Preferred embodiments of the present inventive method will now be illustrated by way of the following non-limiting examples:

EXAMPLE 1

Construction of the *Saccharomyces cerevisiae* Transgenic Strain (XYLUSM21)

*Saccharomyces cerevisiae (USM*21) transformants carrying the xylose reductase (XR) and xylitol dehydrogenase (XDH) genes from the xylose-utilising yeast, *Pichia stipitis*, and the xylulokinase (XK) gene from *Saccharomyces cerevisiae* were constructed. All three genes were placed under control of the PGK promoter-terminator sequences. Competent cells of USM21 were transformed with the linear PstI fragment of YIp2B6, as substantially showed in FIG. 1 in order to integrate a single copy at the locus HIS3 by single crossing-over. Transformed cells were plated on YPX medium.

Xylose-utilising transformants appeared within 4 days at 28° C. Correct integration was verified by Southern analysis and one transformant was retained (strain XYLUSM21).

Mutagenesis:

Ethyl methanesulfonate (EMS) treatment was carried out according to Ausubel et al. ("Current protocols in molecular biology", Vol. 2nd Chap. 13, $1^{st}$ ed. John Wiley & Sons, Inc., 1998, Massachusetts).

Ethyl Methanesulfonate (EMS) Treatment to Obtain Two Mutants (XYL125, XYL145)

The *Saccharomyces cerevisiae* transgenic strain (XYLUSM21) was treated with ethyl methanesulfonate (EMS) to obtain a 20%, 30%, 40%, and 50% survival rate. The treated cells were washed once with 5% sodium thiosulfate and incubated for 10 minutes at room temperature, then the cells were resuspended in sterile distilled water. All cells were transferred together at the same point in time in 50 ml YPD medium complemented with ampicillin (all in one 50 ml YPD medium liquid culture), and incubated for 24 h at 22° C. The culture (XYLUSM21) was transferred 8 times on fresh YPX medium with ampicillin at 24 h intervals and the cell xylose-fermentation was monitored in YPX medium Durham tubes at each 24 h interval. The 2 ml samples which tacked from the culture every 24 h were plated on YPX plates supplemented with ampicillin, and then the colonies which showed a faster grow rate were saved.

From the results of the first screening step, two mutants (XYLUSM125, XYLUSM145) with a faster growth rate than that of the reference strain (XYLUSM21) on YPX medium supplemented with ampicillin were selected and their growth were examined. For shake-flask cultures organisms were pre-grown in 50 ml shake-flasks, containing 10 ml of YPD medium and incubated on a rotatory shaker at 150 rpm and 30° C. for 16 h. These cultures were used to inoculate 500 ml Erlenmeyer flasks, containing 50 ml SCX medium with ampicillin. Cultures were incubated on a rotatory shaker at 150 rpm and 30° C.

Figure 2:
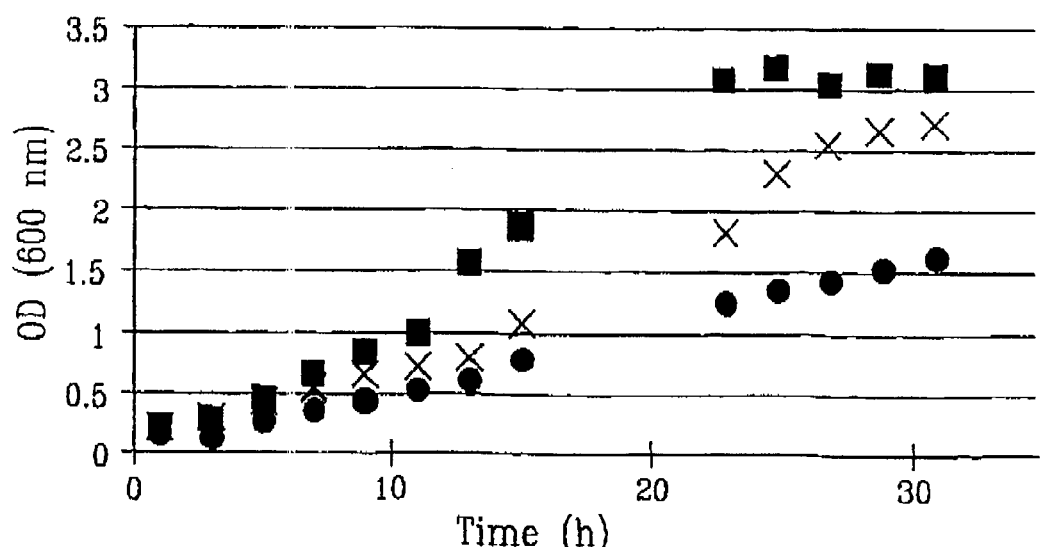
FIG. 2 is a graphical presentation of the present invention, indicating the growth exhibited by two independent xylose-fermenting mutants (XYL125■, XYL145X) and the reference strain (XYLUSM21) in SCX.

Mutants XYLUSM125 and XYLUSM145 showed a 100% and 75% higher growth rate respectively than that of the *Saccharomyces cerevisiae* transgenic strain (XYLUSM21), as showed in FIG. 2. These mutants can effectively use xylose in the absence of other carbon sources.

EXAMPLE 2

Strain and Culture Media:

The wine *Saccharomyces cerevisiae* strain USM21 (Kil+ Gal+) (van der Westhuizen and Pretorius, "The value of electrophoretic fingerprinting and karyotyping in wine yeast breeding programmes", Antonie van Leeuwenhoek 61:249-257, 1992; ZA 91/9818) was employed as the recipients for transformation experiments. Yeast strains were grown in complex medium consisting of 1% yeast extract, 2% peptone, 2% glucose (YPD) or 2% xylose (YPX). To perform the growth curves the strains were grown in synthetic complete (SCX) medium containing 0.67% Difco yeast nitrogen base without amino acids supplemented with 2% xylose as sole carbon source. All the media were complemented with ampicillin at a concentration 100 µg/ml to prevent bacterial contamination.

EXAMPLE 3

Transformation:

*Saccharomyces cerevisiae* was carried out according to Gietz et al. ("Studies on the transformation of intact yeast cells by the LiAc/SS-DNA/PEG procedure", Yeast 11: 355-360, 1995).

EXAMPLE 4

DNA Techniques:

Plasmid DNA was prepared from *Escherichia. Coli* using the CTAB method (Del Sal et al., "A one-tube plasmid DNA mini-preparation suitable for sequencing", Nucleic Acids Res. 16: 9878, 1988). Standard recombinant DNA techniques were performed essentially as described Sambrook et al. ("Molecular cloning: a laboratory manual, 2$^{nd}$ ed. Cold Spring Harbor Laboratory, Cold Spring Harbor, 1989, N.Y.).

EXAMPLE 5

Fermentation

Fermentation has been carried out in a spruce hydrolysate containing. Thereby XYLUSM125 was grown in 20 g/l xylose in minimal medium [Verduyn, C., B. Postma, W. A. Scheffers, and J. P. Van Dijken. 1992. Effect of benzoic acid on metabolic fluxes in yeasts: a continuous-culture study on the regulation of respiration and alcoholic fermentation. Yeast 8:501-507.] and establish XYLUSM125 in a continuous culture on 20 g/l xylose, using a dilution rate of D=0.1 h$^{-1}$ (note, aerobic fermentation, adding oxygen). The growth rate obtained on xylose as only carbon source was Umax=0.14-0.15 h$^{-1}$ and the biomass yield 0.4 g·g$^{-1}$, thus about 8 g/l biomass on 20 g/l xylose as carbon source. When the feed was changed to 20 g/l xylose plus 20 g/l glucose, the biomass raised to 18 g/l and the surprising result was that only 4-5 g/l xylose remained. This indicates that XYLUSM125 simultaneously utilise 20 g/l glucose plus 15-16 g/l xylose in a continuous fermentation at D=0.1 h$^{-1}$.

The experiment was repeated, but this time 20 g/l glucose was first fed to establish a steady state in continuous fermentation, all the glucose was utilized with a biomass yield of about 6 g/l. When the feed was changed to 20 g/l glucose plus 20 g/l xylose, the biomass yield raised to about 14 g/l with all glucose utilized and about 10-12 g/l xylose utilized (thus 8-10 g/l xylose remaining).

The invention claimed is:

1. A recombinant yeast of *Saccharomyces cerevisiae* chosen from XYLUSM125 (deposition number CBS 102679 at Centraalbureau voor Scimmelcultures in Baarn, The Netherlands) and XYLUSM145 (deposition number CBS 102680 at Centraalbureau voor Scimmelcultures in Baarn, The Netherlands), wherein said yeast can grow in a minimum nutrient containing xylose as a sole carbon source and can ferment non-detoxified hydrolysate lignocellulosic raw material.

2. The recombinant yeast of claim 1, wherein the lignocellulosic raw material is a softwood derived hydrolysate.

3. The recombinant yeast of claim 1, wherein the lignocellulosic raw material is a hardwood derived hydrolysate.

4. The recombinant yeast of claim 1, wherein the lignocellulosic raw material comprises both glucose and xylose.

5. The recombinant yeast of claim 1, wherein the lignocellulosic raw material comprises xylose as the sole carbon source.

6. The recombinant yeast of claim 1, wherein the yeast shows a growth rate over *S. cerevisiae* strain USM21, identified as XYLUSM21 (deposition number CBS 102678 at Centraalbureau voor Scimmelcultures in Baarn, The Netherlands) of more than 30%.

7. The recombinant yeast of claim 1, wherein the yeast has a dilution rate of D=0.1 h$^{-1}$ and a growth rate of Umax=0.14-0.15 h$^{-1}$ when grown on xylose as a sole carbon source.

8. The recombinant yeast of claim 1, wherein the yeast yields 0.4 g·g$^{-1}$ biomass when grown on xylose as a sole carbon source under aerobic growth conditions.

9. The recombinant yeast of claim 1, wherein the yeast simultaneously utilizes 20 g/l glucose and 15-16 g/l of xylose in a continuous culture comprising a 20 g/l xylose plus 20 g/l of glucose feed.

10. A method of producing ethanol, said method comprising exposing the recombinant yeast of claim 1 to a medium containing xylose.

11. The method of claim 10, wherein the medium contains glucose and xylose.

12. The method of claim 10, wherein the medium contains xylose as the sole carbon source.

13. The method of claim 10, wherein the medium is a lignocellulosic raw material.

14. The method of claim 13, wherein the lignocellulosic raw material is a softwood derived hydrolysate.

15. The method of claim 13, wherein the lignocellulosic raw material is a hardwood derived hydrolysate.

16. The method of claim 13, wherein the lignocellulosic raw material comprises both glucose and xylose.

17. The method of claim 13, wherein the lignocellulosic raw material comprises xylose as the sole carbon source.

* * * * *

UNITED STATES PATENT AND TRADEMARK OFFICE
CERTIFICATE OF CORRECTION

| | | |
|---|---|---|
| PATENT NO. | : 7,531,348 B2 | Page 1 of 1 |
| APPLICATION NO. | : 10/293255 | |
| DATED | : May 12, 2009 | |
| INVENTOR(S) | : Ricardo Roman Cordero Otero et al. | |

It is certified that error appears in the above-identified patent and that said Letters Patent is hereby corrected as shown below:

Please add the following to the Title Page of the patent:

Related U.S. Application Data

Continuation of application No. PCT/SE01/01061 filed on May 15, 2001.

Foreign Application Priority Data

May 15, 2000 (ZA).................................................... 20002363

Signed and Sealed this

Thirtieth Day of June, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,531,348 B2 | Page 1 of 1 |
| APPLICATION NO. | : 10/293255 | |
| DATED | : May 12, 2009 | |
| INVENTOR(S) | : Ricardo Roman Cordero Otero et al. | |

It is certified that error appears in the above-identified patent and that said Letters Patent is hereby corrected as shown below:

Title page, item (75) ("Inventors"), lines 3-4, "Willhem Herber Van Zyl" should read --Willem Heber Van Zyl--.

Signed and Sealed this

Twenty-eighth Day of July, 2009

JOHN DOLL
*Acting Director of the United States Patent and Trademark Office*